United States Patent [19]

Romero et al.

[11] Patent Number: 5,936,000
[45] Date of Patent: Aug. 10, 1999

[54] 2-AMINOINDANS AS SELECTIVE DOPAMINE D3 LIGANDS

[75] Inventors: Arthur G. Romero; Jeffrey A. Leiby, both of Kalamazoo, Mich.

[73] Assignee: Pharmacia & Upjohn Company, Kalamazoo, Mich.

[21] Appl. No.: 08/860,532

[22] PCT Filed: Jan. 16, 1996

[86] PCT No.: PCT/US96/00020

§ 371 Date: Jun. 20, 1997

§ 102(e) Date: Jun. 20, 1997

[87] PCT Pub. No.: WO96/23760

PCT Pub. Date: Aug. 8, 1996

Related U.S. Application Data

[63] Continuation-in-part of application No. 08/382,239, Feb. 1, 1995.

[51] Int. Cl.$^6$ ..................................................... A01N 33/02
[52] U.S. Cl. ........................... 514/647; 564/308; 564/307
[58] Field of Search .................................. 564/308, 307; 514/647

[56] References Cited

U.S. PATENT DOCUMENTS

| | | | |
|---|---|---|---|
| 4,132,737 | 1/1979 | Molloy | 260/578 |
| 4,829,071 | 5/1989 | Arrowsmith et al. | 514/311 |
| 5,225,596 | 7/1993 | Carlsson et al. | 564/428 |

FOREIGN PATENT DOCUMENTS

| | | |
|---|---|---|
| 88302599 | 3/1988 | European Pat. Off. . |
| WO 90/07490 | 7/1990 | WIPO . |

OTHER PUBLICATIONS

Arneric, SP; Roetker, A; Long, JP; Potent Anorexic–Like Effects of RDS–127 (2–di–n–Propylamino–4,7–Dimethoxyindane) In The Rat: A Comparison with Other Dopamine–Receptor Agonists, Neuropharmacology vol. 21, pp. 885–890, 1982.

Arneric, SP; Roetker, A; Long, JP; Mott, J; Barfknecht, CF; Effects of Semirigid Methoxamine Analogs on Vascular Smooth Muscle: Studies of Methoxy–2–Aminotetralin and 2–Aminoindane Derivatives, Arch. int. Pharmacodyn, 257, 263–273 (1982).

Bhatnagar, RK; Arneric, SP; Cannon, JG; Flynn, J; Long, JP; Structure Activity Relationships of Presynaptic Dopamine Receptor Agonists, Pharmacology Biochemistry & Behavior, vol. 17, Suppl. 1, pp. 11–19, 1982.

Cannon, JG; Furlano, DC; Dushin, RG; Chang, Y; Baird, SR; Soliman, LN; Flynn, JR; Long, JP; Bhatnagar, RK; Assessment of a Potential Dopaminergic Prodrug Moiety in Several Ring Systems, J. Med. Chem., 1986, 29, 2016–2020.

Cannon, JG; Dushin, RG, Long, JP; Ilhan, M; Jones, ND; Swartzendruber, JK; Synthesis and Dopaminergic Activity of (R)–and (S)–4–Hydroxy–2–(di–n–propylamino)indan, J. Med. Chem. 1985, 28, 515–518.

Cannon, JG; Pease, JP; Hamer, RL; Ilhan, M; Bhatnagar, RK; Long, JP; Resorcinol Congeners of Dopamine Derived from Benzocycloheptene and Indan, J. Med. Chem., 1984, vol. 27, No. 2, pp. 186–189.

Cannon, JG; Perez, JA; Bhatnagar, RK; Long, JP; Sharabi, FM; Conformationally Restricted Congeners of Dopamine Derived from 2–Aminoindan, J. Med. Chem. 1982, 25, 1442–1446.

Hacksell, U; Arvidsson, L; Svensson, U; Nilsson, JLG; Monophenolic 2–(Dipropylamino)indans and Related Compounds: Central Dopamine–Receptor Stimulating Activity, J. Med. Chem. 1981, 24, 429–434.

Ma, S; Long, JP; Flynn, JR; Leonard, PA; Cannon, JG, Dopaminergic Structure–Activity Relationships of 2–Aminoindans and Cardiovascular Action and Dopaminergic Activity of 4–Hydroxy, 5–Methyl, 2–di–N–Propylaminoindan (RD–211), Journal of Pharmacology and Experimental Therapeutics, vol. 256, No. 2, pp. 751–756 (1991).

Nichols, DE; Brewster, WK; Johnson, MP; Oberlender, R; Riggs, RM; Nonneurotixic Tetralin and Indan Analogues of 3,4–(Methylenedioxy)amphetamine MDA), J. Med Chem. 1990, 33, 703–710.

**Sindelar, RD; Mott, J; Barfknecht, CF; Arneric, SP; Flynn, JR; Long, JP; Bhatnagar, RK, 2–Amino–4, 7–dimethoxyindan Derivatives: Synthesis and Assessment of Dopaminergic and Cardiovascular Actions, J. Med. Chem. 1982, 25, 858–864.

Patel, "Pharmacotherapy of Cognitive Impairment in Alzheimer's Disease: A Review", J. Geriatr. Psychiatry Neurol. 8:81–95, 1995.

*Primary Examiner*—Dwayne C. Jones
*Attorney, Agent, or Firm*—Donald L. Corneglio; Bruce Stein

[57] ABSTRACT

Compounds and their pharmaceutically acceptable salts suitable for treating central nervous system disorders associated with the dopamine D3 receptor activity of Formula I:

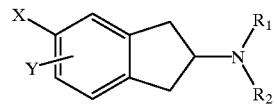

wherein $R_1$ and $R_2$ are independently H, $C_{1-8}$ alkyl or $C_{1-8}$ alkylAryl; X is $CH_2R_3$ or $NHSO_2R_4$; Y is hydrogen, $CH_2R_3$, $NHSO_2R_4$, $CONR_1R_2$, $SO_2NR_1R_2$, $SO_2CH_3$, halogen, $OSO_2CF_3$, $SCH_3$ or $OCH_3$; $R_3$ is $NHSO_2R_4$, $SO_2R_4$, $CONR_1R_2$ or Aryl; and $R_4$ is $NR_1R_2$, $C_1$–$C_8$ alkyl, Aryl or $C_1$–$C_8$ alkylAryl.

6 Claims, No Drawings

2-AMINOINDANS AS SELECTIVE DOPAMINE D3 LIGANDS

This application is a 371 of PCT/US96/00020, filed Jan. 16, 1996 which is a continuation-in-part of U.S. Ser. No. 08/382,239, filed February 1995.

BACKGROUND OF THE INVENTION

The subject invention is directed toward 2-aminoindan analogs that selectively bind to the dopamine D3 receptor in vitro. The dopamine D3 receptor was recently cloned by Sokoloff et al., (Nature, 347, 146 (1990)). It was hypothesized that this receptor subtype is of importance for the action of anti-psychotics. Interestingly, this receptor shows a high abundance in brain regions associated with emotional and cognitive functions.

Compounds with this profile may be useful in treating CNS disorders, e.g. schizophrenia, mania, depression, geriatric disorders, drug abuse and addiction, Parkinson's disease, anxiety disorders, sleep disorders, circadian rhythm disorders and dementia.

Information Disclosure Statement

Arneric, S. P. et al., Neuropharmacol., 21, 885 (1982) describes indan analogs compared with other dopamine agonists. Compounds with 5,6 substitution were found to be inactive in this model of food intake.

Arneric, S. P. et al., Arch. Int. Pharmocodyn. Ther., 257, 263 (1982) describes 2-aminotetralin and 2-aminoindan analogs where the 5,6 dimethoxy substituted compound is again disclosed as inactive agents in an assay to evaluate contractions in vascular smooth muscle.

Bhatnagar, R. K. et al., Pharmacol., Biochem. Behav., 17(Suppl. 1), 11 (1982) discusses SAR studies of various structural entities including aminoindans which interact with dopamine receptors. The 5,6 dimethoxy indans are disclosed as inactive compounds.

Cannon, J. G. et al., J. Med. Chem., 25, 858 (1982) describes 4,7-dimethoxy-2 aminoindans and their dopaminergic and cardiovascular actions.

Cannon, J. G. et al., J. Med. Chem., 25, 1442 (1982) discloses the synthesis of the 5,6 di-methoxy and di-hydroxy indans and also some biology which shows they are devoid of dopamine receptor activity.

Cannon, J. G. et al., J. Med. Chem., 27, 186 (1984) describes the synthesis of N-alkylated derivatives of 2-amino-4,6-dihydroxyindans.

Cannon, J. G. et al., J. Med. Chem., 28, 515 (1985) describes the resolution of the 4-hydroxy aminoindan.

Cannon, J. G. et al., J. Med. Chem., 29, 2016 (1986) describes the ortho OH/methyl, hydroxymethyl, formyl or carboxy derivatives of 2-aminoindans (4,5 substitution), aminotetralins and benz[f] quinolines.

Hacksell, U. et al., J. Med. Chem., 24, 429 (1981) describes the synthesis of monophenolic 2-aminoindans as central dopamine receptor stimulants.

Ma, S. et al., J. Pharmacol. Exp. Ther., 256, 751 (1991) describes dopaminergic structure activity relationships of 2-aminoindans with mainly di-substitution in the 4,5 positions.

Nichols, D. E. et al., J. Med. Chem., 33, 703 (1990) describes nonneurotoxic tetralin and indan analogues of 3,4 (methylenedioxy)amphetamine.

PCT Patent Publication No. WO90/07490 describes 2-aminotetralins and 2-aminoindans with aromatic substitution with an $OCH_3$ or OH in conjunction with a Br group.

European Patent 88302599.1 filed Mar. 24, 1988 discloses antiarrhythmic aminoindanes having a bicyclic structure and methyl group on the amine not disclosed in the subject invention.

U.S. Pat. No. 4,132,737 discloses trifluoromethyl substituted 1-aminoindanes whereas the subject invention is 2-aminoindanes; and U.S. Pat. No. 5,225,596 discloses substituted tetralins although not as substituted herein.

SUMMARY OF THE INVENTION

In one aspect the subject invention is directed toward compounds and pharmaceutically acceptable salts of Formula I:

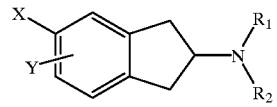

wherein $R_1$ and $R_2$ are independently H, $C_{1-8}$ alkyl, or $C_{1-8}$ alkylAryl;

X is $CH_2R_3$ or $NHSO_2R_4$;

Y is hydrogen, $CH_2R_3$, $NHSO_2R_4$, $CONR_1R_2$, $SO_2NR_1R_2$, $SO_2CH_3$, halogen, $OSO_2CF_3$, $SCH_3$ or $OCH_3$;

$R_3$ is $NHSO_2R_4$, $SO_2R_4$, $CONR_1R_2$ or Aryl; and $R_4$ is $NR_1R_2$, $C_1-C_8$ alkyl, Aryl or $C_1-C_8$ alkylAryl.

In another aspect the subject invention is directed toward compounds and pharmaceutically acceptable salts of Formula I, above, including racemic mixtures and as both enantiomers. Preferred are structures of Formula I where $R_1$ and $R_2$ are independently H and a lower alkyl ($C_{1-8}$ alkyl); and Y is $CONR_1R_2$, $SO_2NR_1R_2$, $SO_2CH_3$ (where $R_1$ and $R_2$ are independently H and a lower alkyl).

In yet another aspect the subject invention is a method for treating schizophrenia by administering a therapeutically effective amount of a compound of Formula I to a patient suffering from schizophrenia.

In yet another aspect, the subject invention is directed toward a method for treating central nervous system disorders associated with the dopamine D3 receptor activity in a patient in need of such treatment comprising administering to the subject a therapeutically effective amount of a Formula I compound for alleviation of such disorder. Typically, the compound of Formula I is administered in the form of a pharmaceutical composition comprising a pharmaceutically-acceptable carrier or diluent.

In yet another aspect, the subject invention is directed toward a pharmaceutical composition for treating central nervous system disorders associated with the dopamine D3 receptor activity comprising an effective amount of a compound of Formula I with a pharmaceutically-acceptable carrier or diluent.

DETAILED DESCRIPTION OF THE INVENTION

The subject invention is directed toward compounds or pharmaceutically acceptable salts of Formula I as depicted above in either racemic or pure enantiomer forms. X, Y, $R_1$, $R_2$, $R_3$ and $R_4$ are independently chosen as listed above.

"Alkyl" are one to eight carbon atoms such as methyl, ethyl, propyl, butyl, pentyl, hexyl, heptyl, octyl and isomeric forms thereof.

Halogen is an atom of fluorine, chlorine, bromine or iodide.

"Aryl" includes benzene and 5- and 6-membered ring aromatic heterocycles containing either one or two of the heteroatoms N, O, S. These aryl groups may be substituted with groups such as H, one or more halogens, CN, $CF_3$, $NO_2$, $C(O)NR_1R_2$, $SO_2NR_1R_2$, $NHC(O)$—$C_{1-3}$alkyl or $SO_2CH_3$.

Pharmaceutically acceptable salts include salts of both inorganic and organic acids. The preferred pharmaceutically acceptable salts include salts of the following acids: methanesulfonic, hydrochloric, hydrobromic, sulfuric, phosphoric, nitric, benzoic, citric, tartaric, fumaric or maleic.

The compounds of Formula I are active orally or parenterally. Orally the Formula I compounds can be given in solid dosage forms such as tablets or capsules, or can be given in liquid dosage forms such as elixirs, syrups or suspensions as is known to those skilled in the art. It is preferred that the Formula I compounds be given in solid dosage form and that it be a tablet.

Typically, the compounds of Formula I can be given in the amount of about 0.25 mg to about 100 mg/person, one to three times a day. Preferably, about 10 to about 50 mg/day in divided doses.

The exact dosage and frequency of administration depends on the particular compound of Formula I used, the particular condition being treated, the severity of the condition being treated, the age, weight, general physical condition of the particular patient, other medication the individual may be taking as is well known to those skilled in the art and can be more accurately determined by measuring the blood level or concentration of the active compound in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar pharmaceutical diluent or carrier materials. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

Chemical Synthesis

Commercially available 4-bromobenzylbromide 1 was alkylated with the lithium enolate of t-butyl acetate (Scheme 1) and subsequently de-esterified with trifluoroacetic acid to give carboxylic acid 2. Conversion to the acyl chloride using thionyl chloride and subsequent Friedel-Crafts cyclization with aluminum chloride gave indanone 3. 6-Bromo-1-indanone 3 was obtained in four steps in 89% overall yield. 6-Bromo-1-indanone 3 was carboxylated using sodium hydride and dimethyl carbonate to give β-keto-methylester 4. A high yield (97%) was obtained on large scale (0.67 mol) using this method. The β-keto-ester was reduced with sodium borohydride and methanol to give the hydroxy-ester, 5.

Dehydration of the β-hydroxy-ester with polyphosphoric acid gave the unsaturated ester 6 in high yield within 60 minutes (Vebrel, J., Carrie, R. Synthese de methoxycarbonylindenes, dihdro-1,2 naphthalenes et benzocycloheptene, Bull. Soc. Chim. Fr., 1982, ptII, 116–24.). De-methylation of the ester was accomplished with aqueous methanesulfonic acid and formic acid (Loev, B., Acid Catalysed Hydrolysis of Esters, Chem. and Ind. 1964, 193–94) to give 7 in high yield. Similar results were obtained using boron tribromide.

Asymmetric hydrogenation with (S)-BINAP-ruthenium (II) diacetate (Ohta, T, et al., Asymmetric hydrogentation of unsaturated carboxylic acids . . . , J. Org. Chem., 1987, 52, 3174–76. and Kitamura, M. et al., Practical synthesis of BINAP-ruthenium dicarboxylate complexes, J. Org. Chem. 1992, 57, 4053–54) afforded 8 in high enantiomeric purity (95:5 ratio). Recrystallization of the (R)-(+)-α-methylbenzylamine/indanoic acid salt from diethyl ether/methanol gave the optically pure acid. Enantiomeric ratios were evaluated by chiral HPLC separation of the reduced acid (alcohol).

At this point carboxylic acid 8 underwent a Curtius rearrangement with the aid of diphenylphosphoryl azide (Ninomiya, K. et al., A new convenient reagent for a modified Curtius reaction, Tetrahed, 1974, 30, 2154–57) to afford t-butyl carbamate 9 which was converted to primary amine 10 by refluxing with trifluoroacetic acid. Dialkylation with bromopropane gave tertiary amine 11. The overall synthesis of (S)-(+)-5-bromo-2-N,N-dipropylaminoindane entails ten steps with a 9% overall yield.

(S)-(+)-5-Bromo-2-N,N-dipropylaminoindane (11) was used as the intermediate for making several enantiomerically pure analogs. A metal halogen exchange with tert-butyllithium afforded the lithium anion, which was treated with trimethylsilylisocyanate to obtain 5-carboxamide analog 12. This was reduced to primary amine 14 with borane-methylsulfide. In a separate series of reactions, the lithium anion of 11 was treated with paraformaldehyde (Rec. Trav. Pays-Bays, 1965, 1200) to obtain the 5-hydroxymethyl analog 13 which was converted to mesylate 15 using methanesulfonyl chloride. This mesylate was then converted to phenyl sulfone 16 using benzenesulfinic acid, sodium salt. It was also converted to acetamide 17, via the acetonitrile, obtained by treating mesylate 15 with sodium cyanide. The acetonitrile intermediate was hydrated using sodium hydroxide and hydrogen peroxide to obtain 17. (Cacchi, S. et al., Amides from nitriles using basic hydrogen peroxide under phase-transfer catalyzed conditions, Synthesis 1980, 243–44.)

Scheme 3 depicts the preparation of compounds 18–22 starting from the 5-hydroxymethyl analog 13. This analog was prepared from 6-Bromo-2-ind-(1-en)oic acid (7) was asymmetrically hydrogenated using (R)-BINAP-ruthenium (II) diacetate to provide (R)-(−)-5-bromoindanoic acid (8). Carboxylic acid 8 underwent a Curtius rearrangement with the aid of diphenylphosphoryl azide to afford t-butyl carbamate 9 which was converted to primary amine 10 by refluxing with trifluoroacetic acid. Dialkylation with bromopropane gave tertiary amine 11. A metal halogen exchange with tert-butyllithium afforded the lithium anion which was treated with paraformaldehyde to obtain the 5-hydroxymethyl analog 13.

(R)-(−)-5-Hydroxymethyl-2-N,N-dipropylaminoindane (13) was converted in 96% yield to the chloromethyl analog 18 using thionyl chloride in tetrahydrofuran (Chem. Rev. 1963, 63, 557). Displacement of chloride with 4-bromothiophenol in basic solution gave (R)-(−)-5-(4-bromobenzene)thiomethyl-2-N,N-dipropylaminoindane (19) in 93% yield. This sulfide was oxidized in 79% yield using peracetic acid to provide sulfone 20. Palladium coupling of formamide with the aryl bromide gave (R)-(−)-5-(4-carboxymidobenzene)sulfonylmethyl-2-N,N-dipropylaminoindane (21). Dehydration of the carboxymide using titanium tetrachloride and triethylamine (Tetrahed. Lett. 1971, 1501) provided the cyano analog 22 in 78% yield.

Scheme 4 depicts the preparation of compounds 24–39 starting with (R)-(−)-5-Bromo-2-N,N-dipropylaminoindane (11) which is lithiated via metal/halogen exchange at the 5-position and treated with diphenylphosphorylazide. The resulting azide was reduced in the same pot with lithium aluminum hydride (Chem. Pharm. Bull. 1986, 1524) to provide (R)-(−)-5-amino-2-N,N-dipropylaminoindane (23) in 41% yield. This primary amine was sulfonylated with benzenesulfonyl chloride or 4-chlorobenzenesulfonyl chloride to give 24 and 25 respectively.

(R)-(−)-5-Bromo-2-N,N-dipropylaminoindane (11) was lithiated via metal/halogen exchange with tert-butyllithium and then treated with trimethylsilylisocyanate to obtain 5-carboxamide analog 12 This was reduced to primary amine 14 with borane-methylsulfide. This primary amine 14 was sulfonylated with various sulfonyl chlorides to give analogs 26 to 39.

Scheme 5 depicts the preparation of compounds 53–56 starting with dimethyl malonate which is dialkylated with propargyl bromide under phase transfer conditions to give the diester 40 which was decarboxylated (A. P. Krapcho and A. J. Lovey, Tetrahed. Lett. 1973, 957; A. P. Krapcho, J. F. Weimaster, J. M. Eldridge, E. G. E. Jahngen, Jr., A. J. Lovey, and W. P. Stephens, J. Org. Chem. 1978, 43, 138) to give the monoester (41). Hydrolysis of the ester with aqueous sodium hydroxide gave the acid (42) which was converted to the t-butylcarbamate (43) via a modified Curtius rearrangment with diphenyl phosphoryl azide (K. Ninomiya, T. Shioiri, and S. Yamada, Tetrahed. 1974, 30, 2151). The t-butylcarbamate was hydrolyzed to 4-amino-1,6-heptadiyne (44) with trifluroacetic acid, and the amine was protected as the trifluroacetamide (45) using trifluoroacetic anhydride and triethylamine in tetrahydrofuran.

The diyne (45) was cyclized with 2-butyne-1,4-diacetate 46 using Wilkinson's catalyst (P. Magnus and D. Witty, Tetrahed. Lett. 1993, 34, 23) in ethanol to give the indane (47). The trifluroacetamide and acetate moieties were hydrolyzed with potassium hydroxide in aqueous methanol to give the crude amine (48) which was dialkylated with 1-bromopropane in acetonitrile to give the dipropylamine (49) in 81% overall yield from 46. The diol (49) was converted to the 5,6-bis(chloromethyl)indane (50) with thionyl chloride.

The 5,6-bis(chloromethyl)indane (50) was converted to the diazide (51) with sodium azide in dimethylformamide. The diazide was not isolated, but was extracted into methy-t-butylether and reduced with lithium aluminum hydride. The reaction showed incomplete reduction and was therefore subjected to magnesium in methanol reduction (S. N. Maiti, P. Spevak, and A. V. Narender Reddy, Syn. Comm. 1988, 18, 1201) to give the crude diamine (52). The diamine was reacted with various sulfonyl chlorides in pyridine to give bis(sulfonamides) 53, 54, and 55.

The 5,6-bis(chloromethyl)indane (56) was converted to the bis(methylphenylsulphone) with sodium benzenesulfinate in dimethylformamide.

EXAMPLES

The procedures are depicted as chemical formulae in Schemes 1–5, following this Example section. The compounds are numbered and represented in the Schemes.

Procedure 1

3-(4-Bromophenyl)propionic Acid. 2 t-Butyl acetate (159 mL, 1180 mmol) was added to lithium diisopropylamide (941 mmol) in tetrahydrofuran at −78° C. followed by 4-bromobenzylbromide (200 g, 784 mmol). The bath temperature was kept at −15° C. for 4 hours whereupon the reaction was quenched with ammonium chloride. The mixture was extracted with diethyl ether and the organic layer was washed with dilute hydrochloric acid, water, and brine, drying with sodium sulfate to yield a pale oil. This was refluxed with trifluoroacetic acid (150 mL, 1960 mmol) for 1 hour. The trifluoroacetic acid was removed under vacuum and the residue was partitioned between diethyl ether and aqueous sodium hydroxide. The aqueous layer was acidified with concentrated hydrochloric acid at 0° C. and extracted with diethyl ether. This organic layer was washed with water and brine and was dried over sodium sulfate to obtain a white solid after removing solvent under vacuum, (167 g, 93%), 132–134° C. m.p.

Procedure 2

6-Bromo-1-indanone. 3

3-(4-Bromophenyl)propionic acid (162 g, 706 mmol) and thionyl chloride (155 mL, 2120 mmol) were refluxed for 90 minutes. The thionyl chloride was then removed under vacuum to yield an amber oil. This oil, aluminum chloride (109 g, 816 mmol), and dichloromethane (1000 mL) were refluxed for 90 minutes and then poured onto ice. Dilute hydrochloric acid was added and the mixture was extracted with diethyl ether. The organic layer was washed with 2N hydrochloric acid, water, aqueous sodium bicarbonate, water, and brine. The product was flash chromatographed on a 25×7 cm silica gel column and eluted with ethyl acetate/dichloromethane (5:95) to obtain a pale brown solid after removing solvent under vacuum, (142 g, 95%), 107–109° C. m.p.

Procedure 3

6-Bromo-2-carboxymethyl-1-indanone. 4

6-Bromo-1-indanone (142 g, 672 mmol) in tetrahydrofuran (1200 mL) was added slowly to refluxing dimethyl carbonate (143 mL, 1680 mmol), sodium hydride (80.6 g, 2020 mmol, 60% in oil, washed with pentane after weighing) and tetrahydrofuran (1200 mL). After refluxing the mixture for 2.5 hours, acetic acid (240 mL) was added dropwise at 0° C. and then allowed to warm to room temp. The mixture was partitioned between diethyl ether/dichloromethane and dilute aqueous hydrochloric acid. The organic layer was washed with 2N hydrochloric acid, water, aqueous sodium bicarbonate, and brine and was then dried over sodium sulfate to obtain a brown solid after removing solvent under vacuum, (176 g, 97%, crude), 124.5–127.5° C. m.p. $^1$H-NMR (300 MHz, CDCl$_3$) (a ratio of approximately 3:1 enol to ketone tautomers) 7.91 (d, 0.27H), 7.77 (d, 0.73H, J=1.8), 7.73 (dd, 0.27H), 7.54 (dd, 0.73H, J=8.1, 1.8), 7.39 (d, 0.27H), 7.34 (d, 0.73H, J=7.9), 3.86 (s, 2.19H), 3.83 (m, 0.27H), 3.80 (s, 0.81H), 3.50 (m, 0.27H), 3.47 (s, 1.46H), 3.32 (m, 0.27H).

Procedure 4

6-Bromo-2-carboxymethyl-1-hydoxyindane. 5

6-Bromo-2-carboxymethyl-1-indanone (139 g, 650 mmol), methanol (1100 mL), and tetrahydrofuran (200 mL) were stirred at 0° C. Sodium borohydride (9.30 g, 245 mmol) was added in portions over 45 minutes and stirred another 45 minutes. More sodium borohydride (12.4 g, 326 mmol) was added in portions over 45 minutes and stirred another 60 minutes. Water was added and the solvent was removed under vacuum at 35° C. The residue was partitioned between diethyl ether and water. The organic layer was washed with water and brine and then dried over sodium sulfate. Flash chromatography of the crude product on a 30×7 cm silica gel column, eluting with dichloromethane/ethyl acetate/hexane (1:2:5), yielded an orange wax (99.6 g, 57%). $^1$H-NMR (300 MHz, CDCl$_3$) (a ratio of approximately 1:1 cis to trans diastereomers) 7.55 (s, 0.43H), 7.51 (s, 0.57H), 7.39 (t, 0.57H, J=8.1), 7.39 (t, 0.43H, J=8.1), 7.13 (d, 0.43H, J=8.1), 7.08 (d, 0.57H, J=8.1), 5.44 (d, 0.57H, J=6.9), 5.30 (d, 0.43H, J=6.0), 3.79 (s, 1.71H), 3.77 (s, 1.29H), 3.45–2.95 (m, 3H), 2.87 (s, 1H).

Procedure 5

6-Bromo-2-carboxymethyl-1-indene. 6

6-Bromo-2-carboxymethyl-1-hydoxyindane, (99.4 g, 367 mmol) was heated with polyphosphoric acid (475 g) for 60 minutes (oil bath temp 70° C., exotherm raising the reaction temp to 80° C.). The reaction was then added to water and extracted with diethyl ether and hexane. The organic layer was washed with water and dilute aqueous sodium bicarbonate and brine and was dried over sodium sulfate to obtain a brown solid after removing solvent under vacuum, (81.0 g, 87%), 93.5–95.0° C. m.p. $^1$H-NMR (300 MHz, CDCl$_3$) 7.64 (m, 2H), 7.45 (dd, 1H, J=8.0, 1.8), 7.37 (d, 1H, J=8.0), 3.85 (s, 3H), 3.64 (d, 2H, J=1.7).

Procedure 6

6-Bromo-2-ind-(1-en)oic Acid. 7

6-Bromo-2-carboxymethyl-1-indene (74.3 g, 293 mmol), methanesulfonic acid (19.3 mL, 293 mmol), formic acid (286 mL, 95%), and water (15 mL) were stirred mechanically under reflux for 6 hours. Diethyl ether, tetrahydrofuran, and water were added and the solution was extracted as a very dilute solution. The organic layer was washed with water and brine. It was mixed with activated carbon for 5 minutes and then filtered through diatomaceous earth. It was dried over sodium sulfate and solvent removed under vacuum to obtain a pale yellow solid, (62.7 g, 89%), 227.5–228.5° C. m.p. $^1$H-NMR (300 MHz, d$_6$ acetone) 7.81 (s, 1H), 7.71 (m, 1H), 7.52 (s, 2H), 3.67 (d, 2H, J=2.0).

Procedure 7

(S)-(+)-5-Bromo-2-indanoic Acid. 8

6-Bromo-2-ind-(1-en)oic acid (29.4 g, 123.0 mmol), crude [(S)-2,2'-bis(diphenylphosphino)-1,1'-binaphthyl] ruthenium (II) diacetate (0.67 mmol), degassed methanol (350 mL), and tetrahydrofuran (35 mL) were shaken under nitrogen (48 PSI) for 63 hrs. The slurry was filtered through diatomaceous earth and solvent was removed under vacuum. The residue was partitioned between diethyl ether and water. The organic layer was basified with 15% aqueous sodium hydroxide. This aqueous layer was acidified with concentrated hydrochloric acid (0° C.) and extracted with diethyl ether/dichloromethane. This organic layer was washed with water and brine, drying over sodium sulfate. Solvent was removed under vacuum to obtain a green solid which was triturated with tetrahydrofuran and petroleum ether. The liquid was decanted off a green solid and solvent was removed under vacuum to obtain brown solid which was recrystallized from toluene and petroleum ether to yield brown solid, (23.2 g, 78%), m.p. 110.0–111.5 ° C. $[\alpha]^{25}_{589}$=+23° (c=0.97 MeOH). $^1$H-NMR (300 MHz, CDCl$_3$) 7.35 (s, 1H), 7.29 (d, 1H, J=8.1), 7.08 (d, 1H, J=8.0), 3.37 (m, 1H), 3.24 (m, 2H), 3.19 (m, 2H). The optical purity was determined by reducing the carboxylic acid to the alcohol (borane dimethylsulfide complex), analyzing this with a Chiracel® OD-H column eluted with isopropanol/hexane (1:20) at 1 mL/min. Unrecrystallized crude product indicates a 95:5 ratio of enantiomers. The acid could be crystallized to optical purity as the (R)-(+)-α-methylbenzylamine salt from methanol and diethyl ether, to obtain white crystals, 155° C. m.p.

Procedure 8

(S)-(+)-5-Bromo-2-[(2-methyl-(2-propoxy)carbonylamino]indane. 9

(S)-(+)-5-Bromo-2-indanoic acid (18.9 g, 78.4 mmol), diphenylphosphoryl azide (21.6 g, 78.4 mmol), t-butanol (80 mL), 1,4-dioxane (80 mL), and triethylamine (10.9 mL, 78.4 mmol) were refluxed for 12 hours. Solvent was removed under vacuum and the residue was partitioned between diethyl ether and water. The organic layer was washed with 2N hydrochloric acid, aqueous sodium bicarbonate, and brine. The solution was dried over sodium sulfate and solvent removed under vacuum to obtain a clear solid. This was flash chromatographed on a 29×5 silica gel column eluting with tetrahydrofuran/hexane (1:10). Solvent was removed under vacuum to obtain a white solid (8.3 g, 34%), 125–126° C. m.p. $[\alpha]^{25}_{589}$=+10° (c=0.95 MeOH).

Procedure 9

(S)-(+)-5-Bromo-2-aminoindane. 10

(S)-+)-5-Bromo-2-[(2-methyl-(2-propoxy)carbonylamino]indane (7.3 g, 23.4 mmol) and trifluoroacetic acid (9 mL, 117 mmol) were refluxed for 60 minutes. The trifluoroacetic acid was removed under vacuum and the residue was partitioned between diethyl ether/tetrahydrofuran and dilute sodium hydroxide. The organic layer was washed with water and brine, drying over sodium sulfate. Solvent was removed under vacuum to obtain a clear oil (4.9 g, 98%). $[\alpha]^{25}_{589}$=+17° (c=1.15 MeOH). $^1$H-NMR (300 MHz, CDCl$_3$) 7.37 (s, 1H), 7.27 (d, 1H, J=8.2), 7.07 (d, 1H, J=7.9), 3.84 (m, 1H), 3.13 (m, 2H), 2.64 (m, 2H), 1.40 (s, 2H).

Procedure 10

(S)-(+)-5-Bromo-2-N,N-di-1-propylaminoindane. 11

(S)-(+)-5-Bromo-2-aminoindane (4.8 g, 22.6 mmol), 1-bromopropane (10.4 mL, 113 mmol), potassium carbonate (6.3 g, 45.3 mmol) and acetonitrile (50 mL) were refluxed for 22 hours. Solvent was removed under vacuum and the residue was partitioned between diethyl ether and water. The organic layer was washed with water and brine and was dried over sodium sulfate. The dark oil was flash chromatographed on a 24×2 cm silica gel column eluting with ethyl acetate/hexane (3:20). Solvent was removed under vacuum to yield a clear oil (5.9 g, 88%). $[\alpha]^{25}_{589}$=+7° (c=1.06 MeOH). The hydrochloride salt was crystallized from methanol and diethyl ether. 220.5–221.5° C. m.p.

Procedure 11

(S)-(+)-5-Carboxamido-2-N,N-dipropylaminoindane. 12 tert-Butyl lithium (12.4 mL of 1.7 M solution in pentane, 21.06 mmol) was added to (S)-(+)-5-bromo-2-N,N-dipropylaminoindane (3.1 g, 10.53 mmol), in tetrahydrofuran (20 mL) at −78° C. After 7 minutes, trimethylsilylisocyanate was added and the cold bath was removed. After 55 minutes, water was added and the mixture was extracted with diethyl ether and aqueous sodium hydroxide. The ether layer was washed with water and brine and was dried over sodium sulfate. Solvent was removed under vacuum to obtain a a pale yellow solid, 97–99° C. m.p. $[\alpha]^{25}_{589}$=+8° (c=1.00 MeOH). The hydrochloride salt was crystallized from methanol and diethyl ether to yield a pale yellow solid (2.19 g, 80%), 283–285° C. m.p.

Procedure 12

(S)-(+)-5-Hydroxymethyl-2-N,N-dipropylaminoindane. 13 tert-Butyl lithium (8.9 mL of 1.7 M solution in pentane, 15.18 mmol) was added to (S)-(+)-5-bromo-2-N,N-dipropylaminoindane (2.25 g, 7.59 mmol), in tetrahydrofuran (12 mL) at −78° C. After 5 minutes, the reaction was added to paraformaldehyde (0.27 g, 8.36 mmol) and tetrahydrofuran (12 mL) at −78° C. After 60 minutes, water was added and the mixture was extracted with diethyl ether and water. The ether layer was washed with water and brine and was dried over sodium sulfate. Solvent was removed under vacuum to obtain a dark brown solid which was flash chromatographed on a 27×2 cm silica gel column, eluting with dichloromethane/ethyl acetate/hexane (1:4:5) and (1:6:3) to obtain 13, amber solid (1.12 g, 60%) 52–54° C. m.p.

Procedure 13

(S)-(+)-5-Aminomethyl-2-N,N-di-1-propylaminoindane. 14

Amide 13 (1.8 g, 6.9 mMol) was dissolved in THF (20 ml) and borane-methylsulfide (2.7 ml of a 10 M solution) was added. This solution was heated to reflux for 1 hr and then cooled. Aqueous 2 N hydrochloric acid (20 ml) was carefully added and the solution was stirred for 2 hr. After neutralization with 2 N sodium hydroxide, the solution was extracted with ether. The ether layer was washed with water and brine, drying over sodium sulfate. Solvent removal afforded the amine as an oil.

Procedure 14

(S)-(+)-5-Methylsulfoxymethyl-2-N,N-dipropylaminoindane. 15

Methanesulfonyl chloride (0.37 mL, 4.67 mmol), 13 (1.05 g, 4.24 mmol), triethylamine (0.71 ml, 5.09 mmol) and dichloromethane (10 mL) were stirred at 0° C. After 2 hours, the mixture was extracted with diethyl ether and aqueous sodium bicarbonate. The ether layer was washed with brine and was dried over sodium sulfate. Solvent was removed under vacuum to obtain an amber oil (1.2 g, 87% crude).

Procedure 15

(S)-(+)-5-Phenylsulfonylmethyl-2-N,N-dipropylaminoindane. 16

Benzenesulfinic acid, sodium salt (0.54 g, 3.23 mmol), 15 (0.35 g, 1.08 mmol), and dimethylformamide (5 mL) were stirred at 50° C. After 24 hours, the mixture was extracted with diethyl ether and aqueous sodium bicarbonate. The ether layer was washed with water and brine and was dried over sodium sulfate. Solvent was removed under vacuum to obtain a dark oil which was flash chromatographed on a 22×1 cm silica gel column, eluting with dichloromethane/ethyl acetate/hexane (1:6:13). Sulfone 16 was obtained as a pale oil (0.12 g, 30%).

Procedure 16

(S)-(+)-5-Carboxamidomethyl-2-N,N-dipropylaminoindane. 17

Sodium cyanide (0.51 g, 9.83 mmol), 15 (0.80 g, 2.46 mmol), and dimethylformamide (5 mL) were stirred at 50° C. After 24 hours, the mixture was extracted with diethyl ether, dichloromethane, and aqueous sodium bicarbonate. The ether layer was washed with water and brine and was dried over sodium sulfate. Solvent was removed under vacuum to obtain a dark oil which was flash chromatographed on a 21×2 cm silica gel column, eluting with dichloromethane/ethyl acetate/hexane (1:3:16), (1:6:15), and then (1:10:9). Solvent was removed under vacuum to yield the cyanomethyl adduct as a dark oil (0.35 g, 55%). This oil was combined with 15% aqueous sodium hydroxide (2.1 mL), tetrahydrofuran (12 mL), and 30% hydrogen peroxide (13.7 mL). After 54 hours, diethyl ether and water were added and the product extracted. The ether layer was washed with water and brine and was dried over sodium sulfate. Solvent was removed under vacuum to obtain a white wax (0.19 g, 59%).

Procedure 17

(R)-(−)-5-Chloromethyl-2-N,N-dipropylaminoindane. 18

Thionyl chloride (2.3 mL) was slowly added to (R)-(−)-5-hydroxymethyl-2-N,N-dipropylaminoindane (7.5 g in 60 mL of dry THF) in an ice bath. After 60 minutes at room temperature, ethanol (5 mL) was added and heated to reflux. Solvent was removed under vacuum and aqueous sodium hydroxide was added the residue. It was extracted with ether. The ether layer was washed with water and brine and was then dried over sodium sulfate. Solvent was removed under vacuum and the residue was flash chromatographed; elution was with ethyl acetate/dichloromethane/hexane to yield an oil.

Procedure 18

(R)-(−)-5-(4-Bromobenzene)thiomethyl-2-N,N-dipropylaminoindane. 19

(R)-(−)-5-Chloromethyl-2-N,N-dipropylaminoindane (3.0 g), 4-bromothiophenol (2.4 g), sodium hydroxide (28 mL of 2N aqueous solution), tetrahydrofuran (28 mL) and a catalytic amount of tetrabutylammonium chloride were heated at 50° C. for 60 minutes. Water was added and the mixture was extracted with ether. The ether layer was washed with water and 2N hydrochloric acid. The acid layer was basified with aqueous sodium hydroxide and extracted with ether/dichloromethane. The organic layer was washed with water and brine and was dried over sodium sulfate. Solvent was removed under vacuum and the residue was flash chromatographed; elution was with ethyl acetate/dichloromethane/hexane to yield a solid, m.p. 80–82° C. The hydrochloride salt, recrystallized from methanol/ether, gave a solid, m.p. 142–144° C.

Procedure 19

(R)-(−)-5-(4-Bromobenzene)sulfonylmethyl-2-N,N-dipropylaminoindane. 20

Peracetic acid (1.7 mL, 32% in acetic acid/water) was added to (R)-(−)-5-(4-bromobenzene)thiomethyl-2-N,N-dipropylaminoindane (1.5 g) in glacial acetic acid (7.5 mL) in a cool water bath. After 4 hours, methyl sulfide (1 mL) was added; after another 30 minutes, ammonium hydroxide (3 M) was added and the mixture was extracted with ether. The ether layer was washed with water and brine and was then dried over sodium sulfate. Solvent was removed under vacuum to yield a solid, m.p. 132–134° C. The maleate salt, recrystallized from methanol/ether, gave a solid, m.p. 130–131° C.

Procedure 20

(R)-(−)-5-(4-Carboxamidobenzene)sulfonylmethyl-2-N,N-dipropyl aminoindane. 21

(R)-(−)-5-(4-Bromobenzene)sulfonylmethyl-2-N,N-dipropylaminoindane (0.94 g), palladium acetate (0.05 g), 1,3-bis(diphenylphosphino)propane (0.21 g), diisopropylethylamine (0.75 mL), dimethylformamide (5 mL), and formamide (0.42 mL) were heated at 120° C. under carbon monoxide. After seven hours, it was cooled to room temperature and sodium hydroxide was added (5 mL, 2N). Water was added and the mixture was extracted with ether/tetrahydrofuran. The ether layer was washed with water and brine and was then dried over sodium sulfate. Solvent was removed under vacuum and the residue was flash chromatographed; elution was with methanol/dichloromethane to yield a solid, m.p. 164–165° C. The fumarate salt, recrystallized from methanol/ether, gave a solid, m.p. 159–163° C.

Procedure 21

(R)-(−)-5-(4-Cyanobenzene)sulfonylmethyl-2-N,N-dipropylaminoindane. 22

Titanium tetrachloride (0.15 mL in carbon tetrachloride, 3 mL) was added to (R)-(−)-5-(4-carboxamidobenzene)sulfonylmethyl-2-N,N-dipropylaminoindane (0.23 g), triethylamine (0.46 mL), and tetrahydrofuran (5 mL) in an ice bath. After 16.5 hours, aqueous sodium carbonate was added and the mixture was extracted with ether. It was washed with brine and dried over sodium sulfate. Solvent was removed under vacuum and the residue was flash chromatographed; elution was with ethyl acetate/dichloromethane/hexane to yield a solid. An analytical sample recrystallized from ethyl acetate/hexane, gave a solid, m.p. 90–91° C. The hydrochloride salt, recrystallized from methanol/ether, gave a solid, m.p. 175° C. (decomposition).

Procedure 22

(R)-(−)-5-Amino-2-N,N-dipropylaminoindane. 23 t-Butyllithium (9.9 mL, 1.7 M in pentane) was added to (R)-(−)-5-Bromo-2-N,N-dipropylaminoindane (11) (2.5 g) in tetrahydrofuran (15 mL) at −78° C. After 5 minutes, diphenylphosphoryl azide (2.0 mL) was added and light was excluded from the reaction vessel. The cold bath was removed and after 45 minutes was reapplied. Lithium aluminum hydride (42 mL, 1.0 N in tetrahydrofuran) was added and the reaction allowed to warm to room temperature. Aqueous hydrochloric acid was added and the mixture was extracted with ether/tetrahydrofuran. The acid layer was basified with 15% sodium hydroxide and extracted with ether/tetrahydrofuran. The organic layer was washed with brine, filtered through diatomaceous earth, and dried over sodium sulfate. Solvent was removed under vacuum and the residue was flash chromatographed; elution was with methanol/dichloromethane to yield an oil.

Procedure 23

(R)-(−)-5-Benzenesulfonamido-2-N,N-dipropylaminoindane. 24

Benzenesulfonyl chloride (0.45 mL) was added to (R)-(−)-5-amino-2-N,N-dipropylaminoindane (0.4 g), triethylamine (0.48 mL), and dichloromethane (5 mL). After 19 hours, ammonium hydroxide (3M aqueous) was added and the mixture was extracted with ether. The ether layer was washed with brine and dried over sodium sulfate. Solvent was removed under vacuum and the residue was flash chromatographed; elution was with ethyl acetate/dichloromethane/hexane to yield 0.51 g of the diphenylsulfonamido adduct. Potassium hydroxide (0.19 g) in methanol (5 mL) and water (0.5 mL) were added. After 17 hours, solvent was removed under vacuum and hydrochloric acid (2N aqueous) was added then was basified with aqueous sodium bicarbonate. The mixture was extracted with ether/dichloromethane and washed with brine, then dried over sodium sulfate. Solvents were removed under vacuum to yield an oil. The hydrochloride salt, recrystallized from methanol/ether, was a solid, m.p. 214–215° C.

(R)-(−)-5-(4-Chlorobenzene)sulfonamido-2-N,N-dipropylaminoindane. 25

Substituting 4-chlorobenzenesulfonyl chloride for benzenesulfonyl chloride, (R)-(−)-5-amino-2-N,N-dipropylaminoindane was treated according to procedure 23 to provide the title compound as an oil. The maleic acid salt, recrystallized from methanol/ether, gave a solid, m.p. 167–169° C.

Procedure 24

(R)-(−)-5-Ethanesulfonamidomethyl-2-N,N-dipropylaminoindane. 26

Ethanesulfonyl chloride (0.2 mL) was added to (R)-(−)-5-aminomethyl-2-N,N-dipropylaminoindane (14) (0.5 g), pyridine (0.3 mL) and tetrahydrofuran (5 mL). After 2.5 hours, ammonium hydroxide was added and the mixture was extracted with ether. The ether layer was washed with water and brine and was then dried over sodium sulfate. Solvent was removed under vacuum and the residue was flash chromatographed; elution was with ethyl acetate/dichloromethane/hexane to yield an oil. The fumarate salt, recrystallized from methanol/ether, gave a solid, m.p. 129–130° C.

(R)-(−)-5-Benzenesulfonamidomethyl-2-N,N-dipropylaminoindane. 27

Substituting benzenesulfonyl chloride for ethanesulfonyl chloride, (R)-(−)-5-aminomethyl-2-N,N-dipropylaminoindane was treated according to procedure 24 to provide the title compound as an oil. The maleate salt, recrystallized from methanol/ether, gave a solid, m.p. 144–145° C.

(R)-(−)-5-(4-Chlorobenzene)sulfonamidomethyl-2-N,N-dipropylaminoindane. 28

Substituting 4-chlorobenzenesulfonyl chloride for ethanesulfonyl chloride, (R)-(−)-5-aminomethyl-2-N,N-dipropylaminoindane was treated according to procedure 24 to provide the title compound as a solid, m.p. 84–87° C.

(R)-(−)-5-(3,4-Dichlorobenzene)sulfonamidomethyl-2-N,N-dipropyl aminoindane. 29

Substituting 3,4-dichlorobenzenesulfonyl chloride for ethanesulfonyl chloride, (R)-(−)-5-aminomethyl-2-N,N-dipropylaminoindane was treated according to procedure 24 to provide the title compound as a solid. Recrystallization from toluene/hexane gave solid m.p. 87–90° C.

(R)-(−)-5-(4-Iodobenzene)sulfonamidomethyl-2-N,N-dipropylaminoindane. 30

Substituting 4-iodobenzenesulfonyl chloride for ethanesulfonyl chloride, (R)-(−)-5-aminomethyl- 2-N,N-dipropylaminoindane was treated according to procedure 24 to provide the title compound as a solid. Recrystallization from ether/hexane gave a solid, m.p. 77–78° C.

(R)-(−)-5-(4-Acetamidobenzene)sulfonamidomethyl-2-N,N-dipropyl-aminoindane. 31

Substituting 4-acetamidobenzenesulfonyl chloride for ethanesulfonyl chloride, (R)-(−)-5-aminomethyl-2-N,N-dipropylaminoindane was treated according to procedure 24 to provide the title compound as a solid. The hydrochloride salt, recrystallized from isopropanol, gave a solid, m.p. 217–218° C.

(R)-(−)-5-(4-Acetamido-3-chlorobenzene)sulfonamidomethyl-2-N,N-dipropyl-aminoindane. 32

Substituting 4-acetamido-3-chlorobenzenesulfonyl chloride for ethanesulfonyl chloride, (R)-(−)-5-aminomethyl-2-N,N-dipropylaminoindane was treated according to procedure 24 to provide the title compound as a solid, m.p. 58–60° C.

(R)-(−)-5-(4-Trifluoromethylbenzene)sulfonamidomethyl-2-N,N-dipropyl-aminoindane. 33

Substituting 4-trifluorobenzenesulfonyl chloride for ethanesulfonyl chloride, (R)-(−)-5-aminomethyl-2-N,N- dipropylaminoindane was treated according to procedure 24 to provide the title compound as a solid, m.p. 66–70° C.

(R)-(−)-5-(4-Nitrobenzene)sulfonamidomethyl-2-N,N-dipropyl-aminoindane. 34

Substituting 4-nitrobenzenesulfonyl chloride for ethanesulfonyl chloride, (R)-(−)-5-aminomethyl-2-N,N-dipropylaminoindane was treated according to procedure 24 to provide the title compound as a solid, m.p. 94–97° C. The hydrochloride salt, triturated with ether, gave a solid.

(R)-(−)-5-(4-Cyanobenzene)sulfonamidomethyl-2-N,N-dipropyl-aminoindane. 35

Substituting 4-cyanobenzenesulfonyl chloride for ethanesulfonyl chloride, (R)-(−)-5-aminomethyl-2-N,N-dipropylaminoindane was treated according to procedure 24 to provide the title compound as solid, m.p. 104–106° C. The fumarate salt, recrystallized from methanol/ether, gave a solid, m.p. 174–177° C.

(R)-(−)-5-(3-Cyanobenzene)sulfonamidomethyl-2-N,N-dipropyl-aminoindane. 36

Substituting 3-cyanobenzenesulfonyl chloride for ethanesulfonyl chloride, (R)-(−)-5-aminomethyl-2-N,N-dipropylaminoindane was treated according to procedure 24 to provide the title compound as an oil. The hydrochloride salt, triturated with ether, gave a solid, m.p. 110° C. (decomposition).

(R)-(−)-5-(2-Cyanobenzene)sulfonamidomethyl-2-N,N-dipropyl-aminoindane. 37

Substituting 2-cyanobenzenesulfonyl chloride for ethanesulfonyl chloride, (R)-(−)-5-aminomethyl-2-N,N-dipropylaminoindane was treated according to procedure 24 to provide the title compound as a solid. The hydrochloride salt, recrystallized from methanol/ether, gave a solid, m.p. 185° C. (decomposition).

(R)-(−)-5-[2-(5-Trifluoro)pyridine]sulfonamidomethyl-2-N,N-dipropyl-aminoindane. 38

Substituting 2-(5-trifluoro)pyridinesulfonyl chloride for ethanesulfonyl chloride, (R)-(−)-5-aminomethyl-2-N,N-dipropylaminoindane was treated according to procedure 24 to provide the title compound as a solid, m.p. 125–127° C. The hydrochloride salt, recrystallized from methanol/ether, gave a solid, m.p. 207–209° C.

(R)-(−)-5-[3-(2,5-Dichloro)thiophenyl]sulfonamidomethyl-2-N,N-dipropyl-aminoindane. 39

Substituting 2,5-dichlorothiophene-3-sulfonyl chloride for ethanesulfonyl chloride, (R)-(−)-5-aminomethyl-2-N,N-dipropylaminoindane was treated according to procedure 24 to provide the title compound as a clear oil. Crystallization from ether/hexane gave a solid, m.p. 79–80° C. The hydrochloride salt, recrystallized from methanol/ether, gave a solid, m.p. 106° C. (decomposition).

Procedure 25

Dimethyl 2,2-di(2-propynyl)malonate. 40

Aqueous sodium hydroxide (1500 ml of a 12 N solution) was placed in a flask fitted with an overhead stirrer. Benzytriethylammonium chloride (54 g) was added and the solution was cooled to 0° C. With vigorous stirring, a solution of dimethylmalonate (79.3 g) and propargyl bromide (3 eq., 214 g) were added with an addition funnel over 25 minutes, keeping the temperature below 25° C. (R. K. Singh, Synthesis 1985, 54). The slurry was then allowed to stir for 3 hr at 25° C. The slurry was then cooled in an ice bath and then carefully added to an ice/water mixture. This was extracted with t-butyl methyl ether, washing the organic layer with water (2x) and then with brine. Drying over sodium sulfate and solvent removal afforded the title compound as a crystalline solid (92% yield).

Procedure 26

Methyl 2-(2-propynyl)-4-pentynoate. 41

Dimethyl 2,2-di(2-propynyl)malonate (71 g) was treated to a Krapcho decarboxylation by heating at 170° C. with with sodium chloride (25 g) and water (23 ml) in dimethylsulfoxide (341 ml). After 15 hr, the solution was cooled and diluted with water and t-butyl methyl ether and extacted. The organic layer was washed with water (4x), brine, and then dried over sodium sulfate. Solvent removal afforded a liquid which was distilled, collecting the title compound at 109° C. (28 mm Hg).

Procedure 27

2-(2-Propynyl)-4-pentynoic Acid. 42

Methyl 2-(2-propynyl)-4-pentynoate (27.5 g) was saponified with sodium hydroxide (22 g) in refluxing water (250 ml). The solution was cooled and acidified with 12 N HCl to pH 3, and then extracted with t-butyl methyl ether. The organic layer was washed with brine and dried over sodium sulfate. Solvent removal afforded the title compound.

Procedure 28

4-(t-Butyloxycarbonylamino)hepta-1,6-diyne. 43

To a solution of 2-(2-propynyl)-4-pentynoic acid 42 (25.0 g, 0.184 mol) in toluene (200 ml) was added triethylamine (19.5 g, 0.193 mol) with cooling. Diphenylphosphoryl azide (50.5 g, 0.184 mol) was added, and the mixture was stirred at room temperature for 15 minutes. The mixture was heated on the steam bath until the reaction became exothermic. When the reaction subsided, the heating was continued for an additional 10 minutes during which time the evolution of gas ceased. Dry t-butanol (150 ml) was added, and the mixture was heated at reflux on the steam bath for 24 hours. The solvent was removed under vacuum, and the residue was diltued with water and extracted twice with diethylether. The combined aqueous extracts were washed with water (2x), 10% sodium carbonate solution, and brine. The solution was dried (MgSO$_4$), and the solvent was removed under vacuum to leave crude 43 as a red-brown solid (35.35 g). A sample (3.2 g) was purified via flash chromatography (230–400 mesh silica gel, 10% ethyl acetate in hexane) to give a colorless solid (2.69 g). Crystallization from hexane gave the title compound (43) as colorless crystals (m.p. 64–67° C.).

Procedure 29

4-Aminohepta-1,6-diyne. 44

The 4-(t-butyloxycarbonylamino)hepta-1,6-diyne 43 (30.28 g, 0.146 mol) was cooled in ice, and trifluoroacetic acid (90 ml) was added with stirring. The mixture was stirred for 20 minutes and the excess trifluoroacetic acid was removed under vacuum. The mixture was partioned be water and diethylether, and the ether solution was extracted twice with 5% hydrochloric acid solution. The combined aqueous extracts were washed with diethylether, cooled in ice, and bascified with solid sodium hydroxide. The mixture was saturated with sodium chloride and extracted 3 times with diethylether. The combined extracts were washed with brine and dried (MgSO$_4$). The solvent was removed under vacuum to leave the title compound (44) as an amber oil (13.2 g, 84%). A sample (0.526 g) was combined with fumaric acid (0.570 g), and the mixture was crystallized from methanol/diethylether to give the fumaric acid salt of 44 as light-yellow crystals (0.694 g, m.p. 178–179° C.).

Procedure 30

4-(Trifluoroacetylamino)hepta-1,6-diyne. 45

A solution of 4-aminohepta-1,6-diyne 44 (14.63 g, 0.137 mol) and triethylamine (20.8 g, 0.206 mol) in dry tetrahydrofuran (100 ml) was cooled in ice and trifluoroacetic anhydride (37.5 g, 0.178 mol) was added via a syringe pump over a perion of 30 minutes. The mixture was stirred at 0° C. for 1 hour and allowed to stand at −15° C. overnight. The mixture was cooled in ice, and water (100 ml) was added dropwise. The mixture was extracted twice with diethylether. The combined organic extracts were washed with 10% hydrochloric acid, saturated sodium bicarbonate solution (2×) and brine. The solution was dried (MgSO$_4$), and the solvent was removed under vacuum to leave a solid (29.6 g). Cyrystallization from hexane containing a little ethyl acetate gave 45 as slightly yellow crystals (21.5 g, m.p. 55–57° C.).

Procedure 31

2-(Trifluoroacetylamino)-5,6-bis(acetoxymethyl) indane. 47

A solution of 2-butyne-1,4-diacetate 46 (34.03 g, 0.200 mol) and tris(triphenylphosphine)rhodium chloride (2.78 g, 3.00 mmol, 3 mol %) in argon degassed ethanol (100 ml) was heated to 80° C., and a solution of 4-(trifluoroacetylamino)hepta-1,6-diyne (20.32 g, 0.100 mol) in argon degassed ethanol (70 ml) was added via a syringe pump over a 2.5 hour period. The mixture was stirred at 75–80° C. for 8 hours and at room temperature for 10 hours. The solvent was removed under vacuum to leave a dark oil. Purification by flash chromatography (230–400 mesh silica gel, 25–30% ethyl acetate/hexane) gave an amber solid (24.5 g). Crystallization from ethyl acetate/hexane gave the title compound (47) as tan crystals (22.0 g, 59%, m.p. 98–100° C.).

Procedures 32 and 33

2-(N,N-Dipropylamino)-5,6-bis(hydroxymethyl) indane. 49

A solution of potassium hydroxide (10.10 g, 0.180 mol) in water (35 ml) was added to a solution of 2-(trifluoroacetylamino)-5,6-bis(acetoxymethyl)indane 47 (20.1 g, 53.8 mmol) in methanol (200 ml) at room temperature, and the mixture was heated to reflux for 2.5 hours. The solvent was removed under vacuum to leave 2-amino-5,6-bis(hydroxymethyl)indane (48) as a semisolid. The crude product was mixed with 1-bromopropane (27.1 g, 0.220 mol) and potassium carbonate (22.32 g, 0.162 mol) in acetonitrile (100 ml), and the mixture was stirred mechanically at reflux on the steam bath for 17 hours. 1-Bromopropane (6.8 g, 0.055 mol) was added, and the reflux was continued for 4 hours. The mixture was diluted with water and extracted twice with ethyl acetate. The extracts were washed with brine and dried (MgSO$_4$). The solvent was removed under vacuum to leave a brown oil (15.75 g). Purification by flash chromatography (230–400 mesh silica gel, ethyl acetate to 30% tetrahydrofuran in ethyl acetate) gave the title compound (49) as a solid (12.1 g, 81%). A sample (0.50 g) was crystallized from ethyl acetate/hexane to give white crystals (0.48 g).

Procedure 34

2-(N,N-Dipropylamino)-5,6-bis(chloromethyl) indane. 50

2-(N,N-Dipropylamino)-5,6-bis(hydroxymethyl)indane 49 (2.78 g, 10.0 mmol) was cooled in ice and thionyl chloride (8.0 ml) was slowly added. The mixture was heated to reflux on the steam bath for 1.25 hours. The excess thionyl chloride was removed under vacuum. The residue was dissolved in chloroform, and the solvent was removed under vacuum. This was repeated giving an amber solid. The compound was stirred with a mixture of 10% sodium carbonate solution and tetrahydrofuran until all the solid had dissolved. The mixture was extracted twice with diethylether, and the combined extracts were washed with brine and dried (MgSO$_4$). The solvent was removed under vacuum to leave the title compound (50) as an oil (3.46 g).

Procedures 35 and 36

2-(N,N-Dipropylamino)-5,6-bis(aminomethyl) indane. 52

Sodium azide (3.30 g, 50.8 mmol) was added to a solution of 2-(N,N-dipropylamino)-5,6-bis(chloromethyl)indane 50 (2.85 g, 9.07 mmol) in dimethylformamide (35 ml) at room temperature, and the mixture was stirred at 80° C. overnight. The mixture was diluted with water and extracted three times with methy-t-butylether. The combined extracts were washed twice with water and once with brine. The solution was dried (MgSO$_4$) and filtered. The solution containing 2-N,N-dipropylamino)-5,6-bis(azidomethyl)indane 51 was cooled in ice, and lithium aluminum hydride (1.0 M in tetrahydrofuran, 13 ml, 13 mmol) was slowly added, and the resulting reaction was stirred at room temperature for 2 hours. Water (0.5 ml), 15% sodium hydroxide (0.5 ml), and water (1.5 ml) were added in succession. The mixture was stirred for 30 minutes and filtered. The aluminum salt was washed with tetrahydrofuran, and the combined filtrate was evaporataed giving an amber oil (2.27 g). The compound was dissolved in methanol (100 ml) and magnesium metal (2.5 g) was added. The mixture wa heated on the steam bath until the reaction became exothermic. The the magnesium was depleted, the solvent was removed under vacuum to leave a solid. The mixture was suspended in water and extracted several times with 1:1 tetrahydrofuran/diethylether (emulsion). The combined extracts were washed with brine and dried (MgSO$_4$). The solvent was removed under vacuum to leave the title compound (52) as a brown oil (0.92 g).

Procedure 37

2-(N,N-Dipropylamino)-5,6-bis(4-chlorophenylsulfonylaminomethyl)indane. 53

A solution of 2-(N,N-dipropylamino)-5,6-bis (aminomethyl)indane 52 (0.276 g, 1.00 mmol) in pyridine (4.0 ml) was cooled in ice, and 4-chlorobenzenesulfonyl chloride (0.53 g, 2.51 mmol) was added. The mixture was stirred at 0° C. for 40 minutes and at room temperature for 18 hours. Water was added, and the mixture was stirred at room temperature for 1 hour. The mixture was diluted with 10% sodium carbonate solution and extracted twice with diethylether and once with ethyl acetate. The combined extracts were washed with brine and dried (MgSO$_4$). The solvent was removed under vacuum to leave a red-brown oil (0.34 g). Purification by flash chromatography (230–400 mesh silica gel, 60% ethyl acetate/hexane) gave an orange solid. Crystallization from diethylether/hexane gave the title compound (53) as slightly orange crystals (0.090 g, m.p. 140–141° C.).

Procedure 38

2-(N,N-Dipropylamino)-5,6-bis(4-cyanophenylsulfonylaminomethyl)indane. 54

A solution of 2-(N,N-dipropylamino)-5,6-bis (aminomethyl)indane 52 (0.276 g, 1.00 mmol) in pyridine (4.0 ml) was cooled in ice, and 4-cyanobenzenesulfonyl chloride (0.61 g, 3.0 mmol) was added. The mixture was stirred at room temperature for 4 hours. The mixture was diluted with 10% sodium carbonate solution and extracted three times with ethyl acetate. The combined extracts were washed with brine and dried (MgSO$_4$). The solvent was removed under vacuum to leave a dark oil. Purification by flash chromatography (230–400 mesh silica gel, 60–80% ethyl acetate/hexane) gave the title compound (54) as an oil. The compound was dissolved in ethyl acetate and excess ethereal hydrochloric acid was added. The mixture was diluted with diethylether and filtered. The precipitate was washed with diethylether and dried under vacuum giving the hydrochloride salt of 54 as a tan solid (0.143 g).

Procedure 39

2-(N,N-Dipropylamino)-5,6-bis(S-propylsulfonylaminomethyl)indane. 55

A solution of 2-(N,N-dipropylamino)-5,6-bis (aminomethyl)indane 52 (0.36 g, 1.3 mmol) in pyridine (5.0 ml) was cooled in ice, and 1-propanesulfonyl chloride (0.64 g, 4.5 mmol) was added. The mixture was stirred at 0° C. for 30 minutes and at room temperature for 3 hours. Water (15 ml) was added, and the mixture was stirred at room temperature for 15 minutes. The mixture was diluted with 10% sodium carbonate solution and extracted three times with with diethylether. The combined extracts were washed with brine and dried (MgSO$_4$). The solvent was removed under vacuum to leave a brown oil (0.51 g). Purification by flash chromatography (230–400 mesh silica gel, 80% ethyl acetate/hexane) gave a yellow oil 0.131 g. Crystallization from diethylether/hexane gave the title compound (55) as off-white crystals (0.092 g, m.p. 120–121° C.).

Procedure 40

2-(N,N-Dipropylamino)-5,6-bis (phenylsulfonylmethyl)indane. 56

The title compound (56) was prepared from 2-(N,N-dipropylamino)-5,6-bis(chloromethyl)indane and sodium benzenesulfinate in dimethylformamide at 100° C. The free base is converted to the fumaric acid salt with fumaric acid (m.p. 160–168° C.).

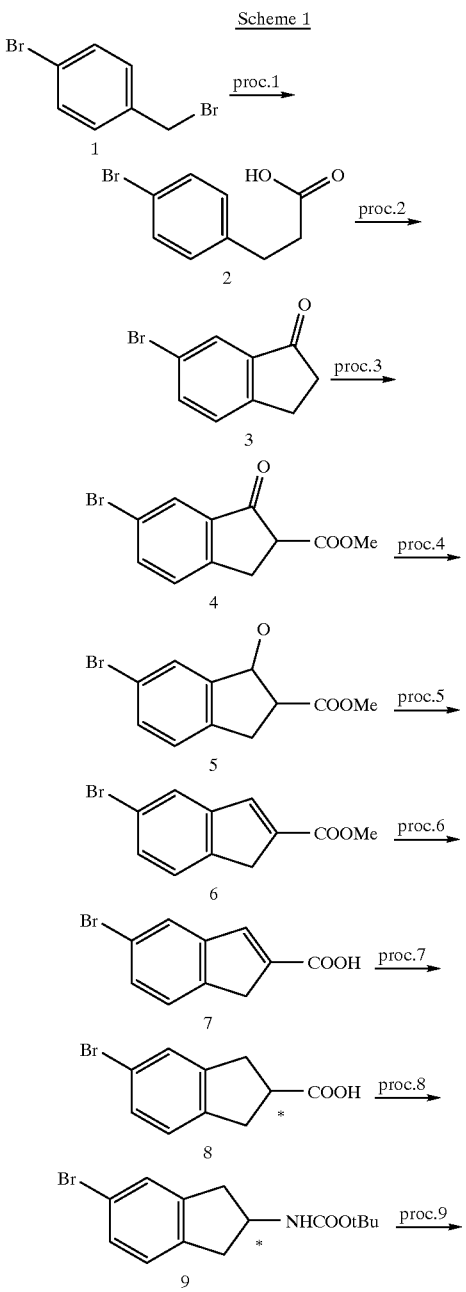

Scheme 1

-continued
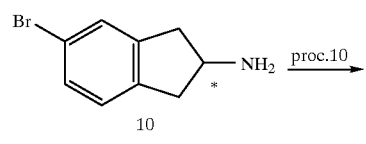
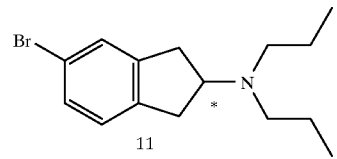
Scheme 2
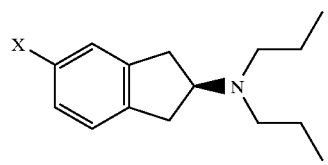
| Proc. | X | Compound # |
|---|---|---|
| 11 | CONH2 | 12 |
| 12 | CH2OH | 13 |
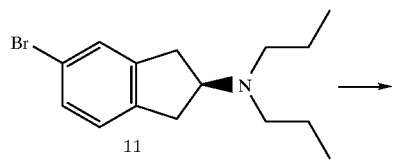
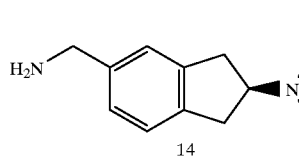
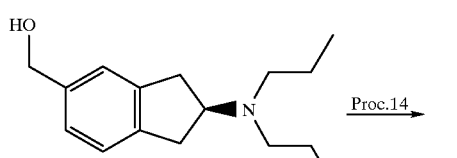
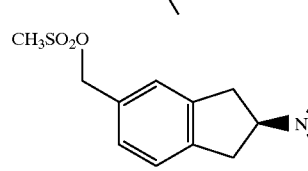
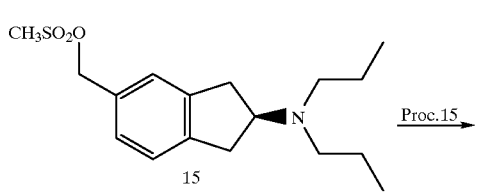
-continued
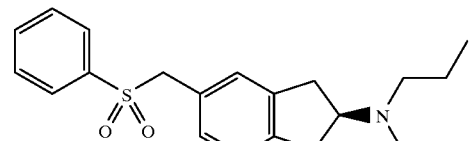
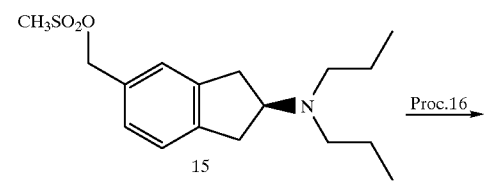
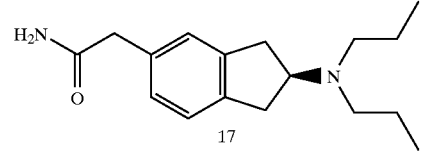
Scheme 3
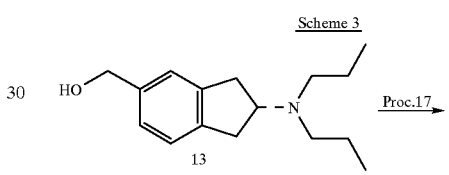
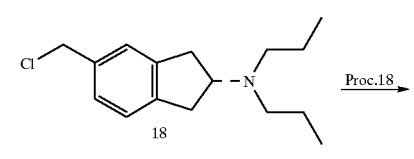
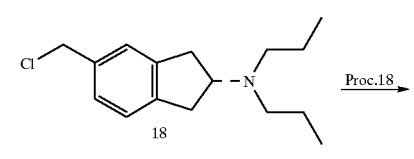
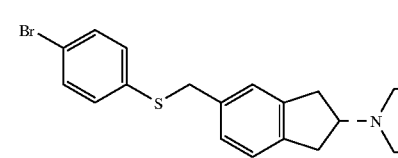
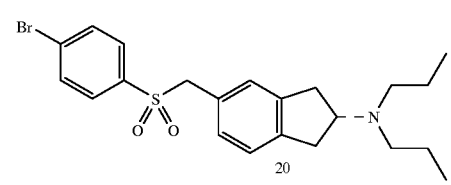

23
-continued
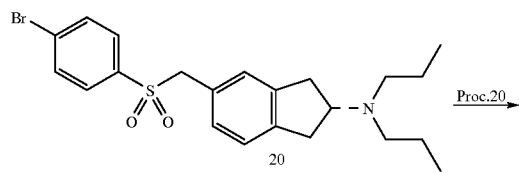
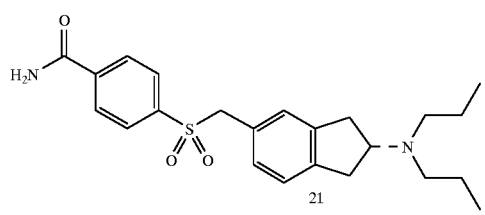
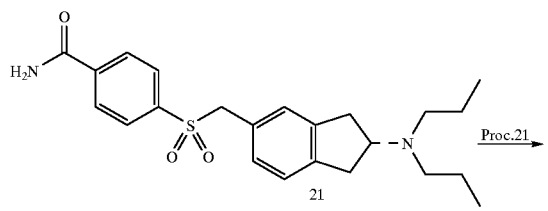
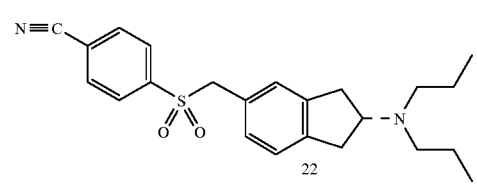
Scheme 4
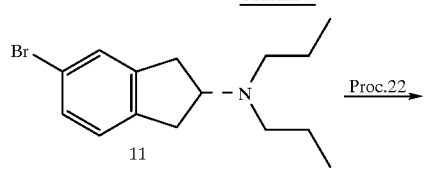
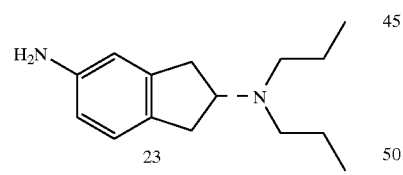
24
-continued
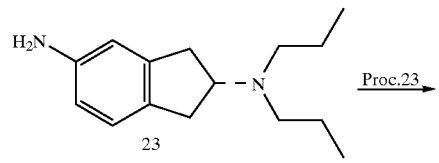
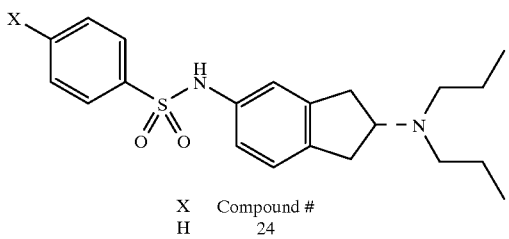
| X | Compound # |
|---|---|
| H | 24 |
| Cl | 25 |
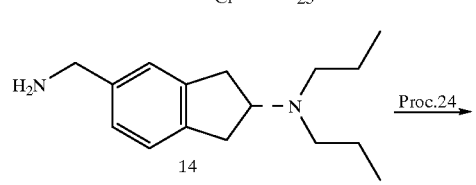
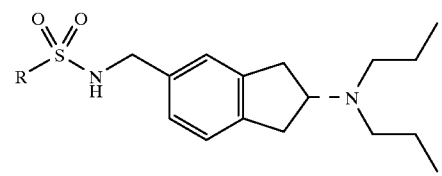
| R | Compound # |
|---|---|
| CH$_3$CH$_2$ | 26 |
| Ph | 27 |
| 4-Cl Ph | 28 |
| 3-Cl, 4-Cl Ph | 29 |
| 4-IPh | 30 |
| 4-AcNHPh | 31 |
| 3-Cl, 4-AcNHPh | 32 |
| 4-CF$_3$Ph | 33 |
| 4-NO$_2$Ph | 34 |
| 4-NCPh | 35 |
| 3-NCPh | 36 |
| 2-NCPh | 37 |
| 2-(5-CF$_3$)pyridyl | 38 |
| 3-(2-Cl, 5-Cl)thiophenyl | 39 |
Scheme 5
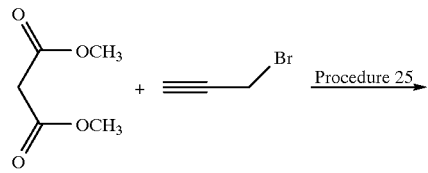

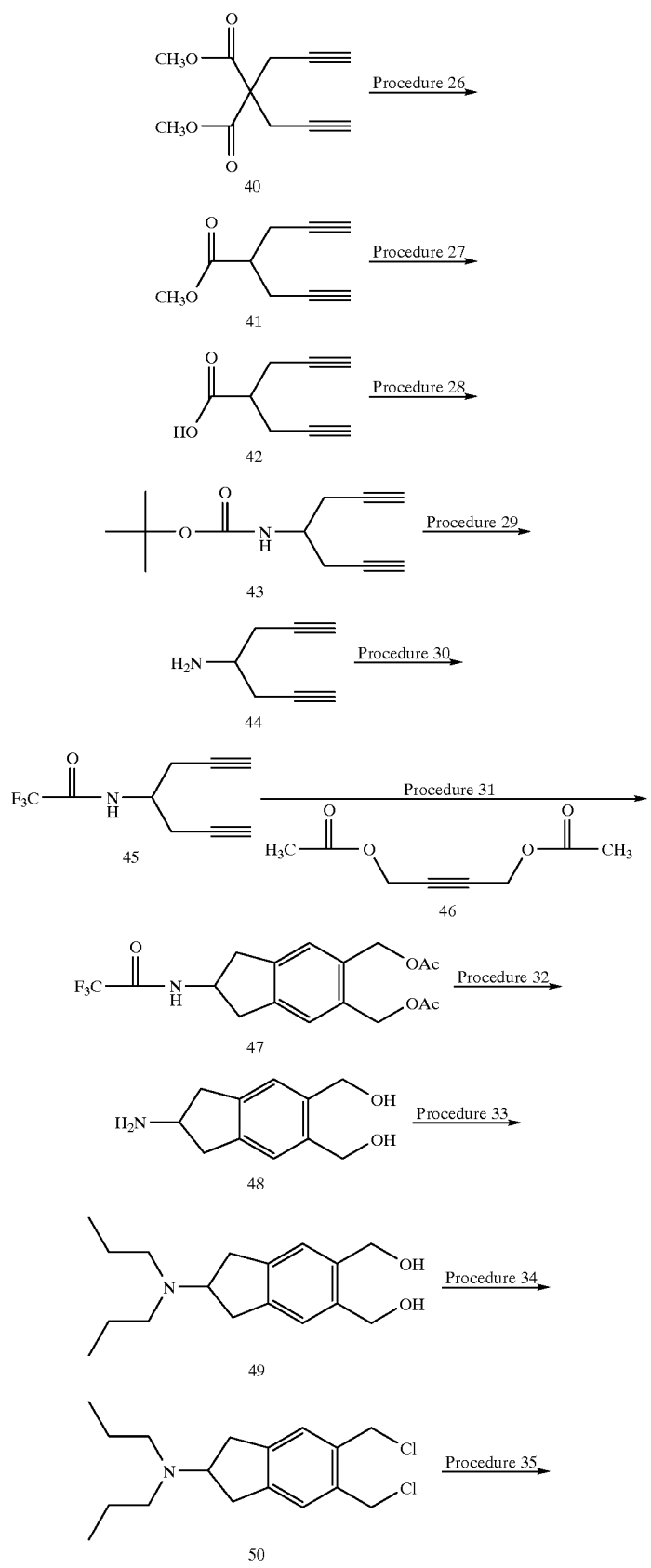

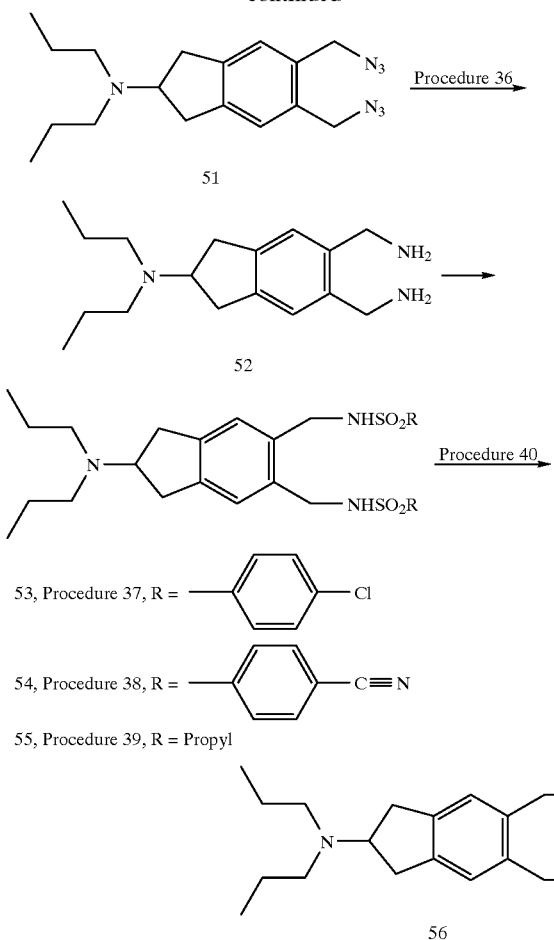

What is claimed:

1. A compound of Formula I or its pharmaceutically acceptable salts

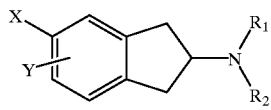

wherein $R_1$ and $R_2$ are independently H, $C_{1-8}$ alkyl or $C_{1-8}$ alkylAryl;

X is $CH_2R_3$ or $NHSO_2R_4$;

Y is hydrogen, $CH_2R_3$, $NHSO_2R_4$, $CONR_1R_2$, $SO_2NR_1R_2$, $SO_2CH_3$, halogen, $OSO_2CF_3$, $SCH_3$ or $OCH_3$;

$R_3$ is $NHSO_2R_4$, $SO_2R_4$, $CONR_1R_2$ or Aryl; and $R_4$ is $NR_1R_2$, Aryl or $C_1$–$C_8$ alkylAryl with the proviso that when X is $NHSO_2R_4$ and $R_4$ is Aryl where Aryl is benzene, then benzene must be substituted with either —CN, —$CF_3$, —$NO_2$, —CO—$NR_1R_2$, —NH—CO-alkyl, —$SO_2$—$CH_3$.

2. The compound of claim 1 wherein Y is $CONR_1R_2$, $SO_2NR_1R_2$ or $SO_2CH_3$.

3. The compound of claim 2 wherein $R_1$ and $R_2$ are independently H or $C_{1-8}$ alkyl.

4. The compound of claim 1 wherein $R_1$ and $R_2$ are independently H or $C_{1-8}$ alkyl.

5. The compound of claim 1 wherein $R_4$ is $C_{1-8}$ alkyl.

6. The compound of claim 1 wherein $R_3$ is $CONR_1R_2$ and $R_1$ and $R_2$ are independently H or $C_{1-8}$ alkyl.

* * * * *